United States Patent [19]

Mohr et al.

[11] Patent Number: 4,493,318

[45] Date of Patent: Jan. 15, 1985

[54] LOCKING MECHANISM FOR USE WITH TWO ANESTHETIC EVAPORATORS

[75] Inventors: Helmut Mohr, Lübeck; Wolfgang Falb, Krummesse; Carl F. Wallroth, Lübeck, all of Fed. Rep. of Germany

[73] Assignee: Drägerwerk Aktiengesellschaft, Fed. Rep. of Germany

[21] Appl. No.: 486,099

[22] Filed: Apr. 18, 1983

[30] Foreign Application Priority Data

Nov. 6, 1982 [DE] Fed. Rep. of Germany ....... 3222047

[51] Int. Cl.$^3$ ............................................ A61M 16/00
[52] U.S. Cl. ............................ 128/200.19; 74/483 K; 261/DIG. 65; 137/637.1; 137/614.06; 128/200.14; 251/149.9
[58] Field of Search .................... 128/200.14, 200.19; 74/483 K, 483 R; 137/637.1, 614.06; 261/DIG. 65; 251/111, 113, 149.9

[56] References Cited

U.S. PATENT DOCUMENTS

| | | | |
|---|---|---|---|
| 4,307,718 | 12/1981 | Schreiber | 128/200.14 |
| 4,308,865 | 1/1982 | Hay | 128/200.14 |
| 4,346,701 | 8/1982 | Richards | 128/200.14 |
| 4,434,790 | 3/1984 | Olesen | 128/200.14 |

Primary Examiner—Henry J. Recla
Attorney, Agent, or Firm—McGlew and Tuttle

[57] ABSTRACT

A locking mechanism for use with two evaporators comprises first and second anesthetic evaporators each having a respective rotatable first and second side-by-side opening valve disc with a radially extending opening therein with an arm located between the disc which has a transverse bore therethrough. The cylindrical latch is slidable in the bore and has an accommodation recess adjacent each of its ends at aligned diametrical locations. A control pin is carried by each of the discs and enters into the opening at one diametrical location and is of a size to be accommodated within the accommodation recess of the latch when the pin and the opening are properly aligned with the accommodation recess of the latch. The latch is positionable in the opening of either selected disc with the pin accommodated within the accommodation recess in a position at which its opposite end frees the other disc for rotation for opening its associated evaporator. The latch is also positionable between the disc so that its respective ends into each opening of each disc to lock both of the discs to prevent opening of both evaporators.

4 Claims, 3 Drawing Figures

LOCKING MECHANISM FOR USE WITH TWO ANESTHETIC EVAPORATORS

BACKGROUND OF THE INVENTION

Field of the Invention

This invention relates, in general, to anesthetizers and, in particular, to a new and useful locking mechanism for the evaporators of anesthetizers.

The anesthetizers contain generally two evaporators in which various anesthetics are evaporated, and the vapor is then fed in adjusted amount to the respiratory system of the patient. In replaceable evaporators, which are simply suspended, a plurality of anesthetics may be available.

For safety reasons, it is necessary to provide a locking mechanism which prevents that the user accidentally opens either the wrong evaporator or both evaporators.

A Wknown locking system for an evaporator-anesthetizer with two evaporators has a three-way selector valve with which one of the evaporaors can be selected in its outside positions, while the other is locked in its zero position. Evaporator and selector valve are arranged at the front end of a distributor designed as a carrier which has an interior with respective gas paths. Each evaporator is suspended detachably by means of an angle over pairs of pins on the top side of the distributor. Gas apertures on the back of the evaporator are in contact with gas apertures at the front end of the distributor. On its top side are pivotally mounted two latches designed as rocking arms, which move against tension springs. In the stretched position, one end reaches behind the end of a locking flange on the adjusting knob of the respective evaporator and locks the latter in the zero position. In the relaxed position of the latch, the locking flange is free and the adjusting knob, hence the evaporator, can thus be freely operated. A link connected with the selector valve controls the latches at their other end, so that one latch is in the relaxed condition in the outside position, and the other is in the stretched condition. In the center position, both latches are in the stretched condition. This locking system is elaborate and susceptible to trouble, due to its many parts. The angle for the suspension of the evaporator must be introduced between a pair of retaining pins and the latch (DE-OS 30 58 564).

Another safety device for an anesthetizer with evaporators arranged in pairs is known which has the effect that one evaporator is locked when the other evaporator is in the open position.

Each evaporator has a rotating dial to determine the vapor concentration to be given off. The safety device contains a pair of reciprocating sensing pins and a swivel level cooperating with them. Each sensing pin is so arranged that it engages a cam recess in the dial when it is moved there by a corresponding swivel movement of the swivel lever. This dial is thus blocked and the evaporator cannot be connected.

The rotary movement of one dial causes automatically the sensing pin engaging the cam recess to move outside this cam recess, and causes a swivel movement of the swivel lever with which the other sensing pin is then introduced into the cam recess of the dial of the other evaporator. The mechanically relatively simple design permits only the use of anesthetizers with fixedly mounted evaporators. Its use with replaceable evaporators is not possible. (DE-OS 31 01 434).

SUMMARY OF THE INVENTION

The invention provides a mechanically simple and reliable locking mechanism in anesthetizers with evaporators arranged in pairs which ensures that only one evaporators can be opened and remain open, or that both evaporators are locked.

In accordance with the invention, two anesthetizer evaporators are arranged side by side between an arm which extends between rotatable side-by-side opening valve discs of the associated evaporators which have an opening extending diametrically therethrough. The arm which is located between the discs have a transverse bore and a cylindrical latch is slidable in the bore and has an accommodation recess adjacent each end at aligned diametric locations. A control pin is carried by each of the disks and it enters into the opening of the disk at a sized diametric location. Control pins are of the size to be accommodated within the combination recess of the associated end of the latch when the opening of the disk and the control pin are aligned with the recess of the latch. The latch is positionable in an opening of either selected disk and in such position the control pin is accommodated within the accommodation recess and locks the associated disk. In such a position, the other disk is free for rotation for opening its associated evaporator. The latch is also positionable between the disk so that it locks its disk and prevents its rotation.

The design of the locking mechanism ensures, particularly in anesthetizers with simple replacement of the evaporators by suspension, that only one evaporator can be opened and then remain open. The position of the journal in which the engagement of the disk of the handwheel of the respective evaporator can be seen shows clearly that this evaporator is locked. Only the handwheel of the other evaporator turns. Switching is only possible after this evaporator is locked after the zero position of its handwheel and by pushing-in its slide. The handwheel of the other evaporator is then released.

The through-opening of the annular disks on the handwheels with the pin protruding on the same side permits the evaporator to be suspended during the replacement, both on one and on the other side. The operation of the locking mechanism is not hindered.

In one embodiment of the invention, it is possible to lock both evaporators by the center position of the latch, because neither handwheel can be turned.

Accordingly, it is an object of the invention to provide an improved locking arrangement for the operation of two anesthetic evaporators which includes means for permitting selective use of only one of the rotatable valves of the evaporators to open the evaporator or an arrangement in which both of the valves are locked.

A further object of the invention is to provide an anesthetic evaporator locking device which is simple in design, rugged in construction and economical to manufacture.

For an understanding of the principles of the invention, reference is made to the following description of a typical embodiment thereof as illustrated in the accompanying drawings.

GENERAL DESCRIPTION OF THE PREFERRED EMBODIMENTS

Figure 1:
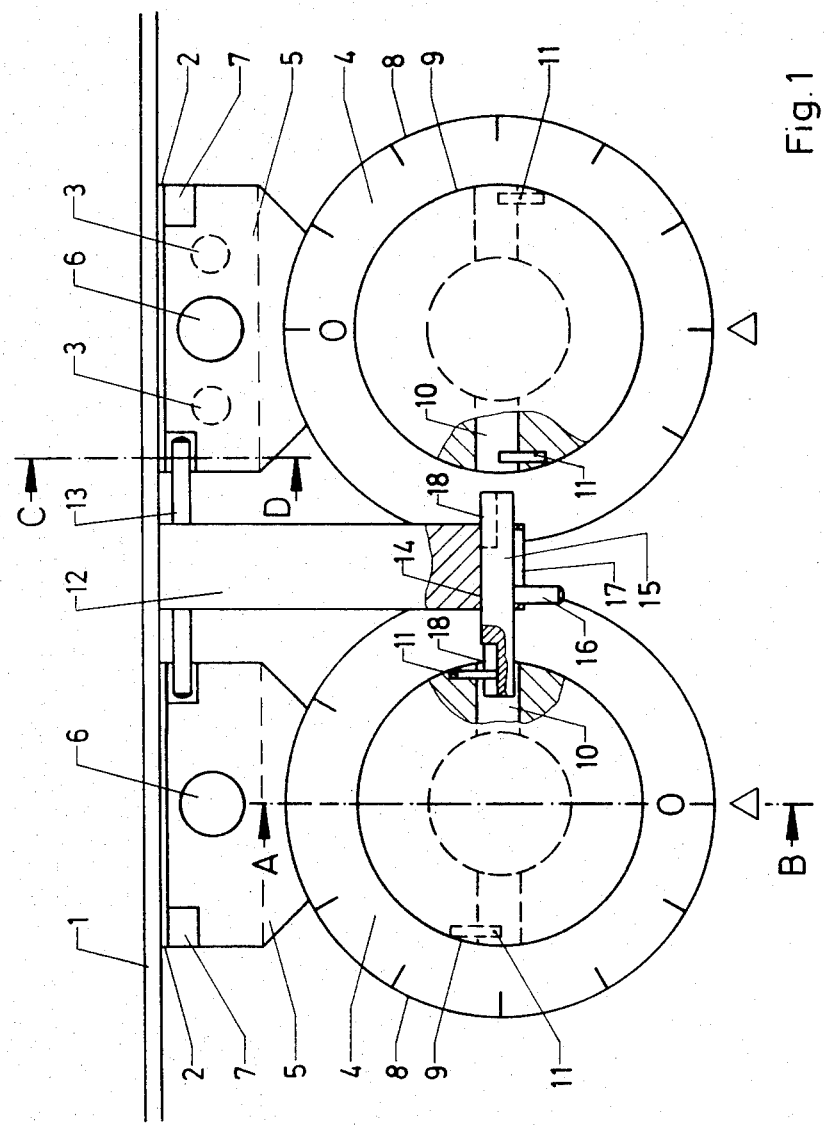
FIG. 1 is a top view, partly in section, of two evaporators having a locking mechanism connected thereto permitting locking of both the evaporators or the selected use of only one evaporator as constructed in accordance with the invention.
Figure 2:
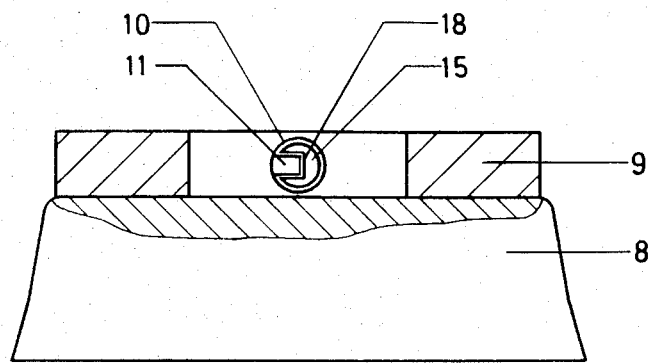
FIG. 2 is an enlarged sectional view taken along the lines A—B of FIG. 1.

Referring to the drawings, in particular, the invention embodied therein comprises a locking mechanism for use with two anesthetic evaporators arranged side-by-side and having respective rotatable first and second side-by-side opening valve discs 9, 9 associated with respect to the evaporators 4,4. Each valve disk 9 has a radially extending opening 10 which, in the embodiment shown, extends to the complete diameter of the associated disk. An arm 12 is located between the disk and has a transverse bore 14 in which a cylindrical latch 15 is slidable. Latch 15 has an accommodation recess 18 adjacent each end which are at aligned diametrical locations. The control pin 11 is carried by each disk 9 and enters into an associated opening 10 at one diametric location and they are of a size to be accommodated within the accommodation recess 18 of the latch 15 when the opening 10 of the associated disk 9 is correctly oriented in respect to the associated control pin 11 which, in the embodiment of the invention illustrated is when the control valves are at the closed or zero opening position as indicated on a scale handwheel 8. The latch 15, in accordance with the invention, is positionable in the opening 10 of either selected disk 9 when the control pin 11 is accommodated in the combination recess and this will cause locking of the associated disk 9. In the position indicated in FIG. 1, the disk 9 on the left-hand side is locked and the other disk 9 is free for rotation for opening its associated evaporator 4. The latch 15 may also be positioned so that it extends into the right-hand opening 10 of the associated disk 9 only when the disk is first moved to a zero-indicating position in which the valve of the evaporator would be closed. The latch 15 may be moved all the way into the associated opening in order to free the opposite disk, for example, the disk on the left-hand side in another position of operation. Lastly, the latch 15 may be positioned so that it engages into an opening 10 of each of the disks and thus locks both of them against the rotation and opening of the associated evaporator 4.

Figure 3:
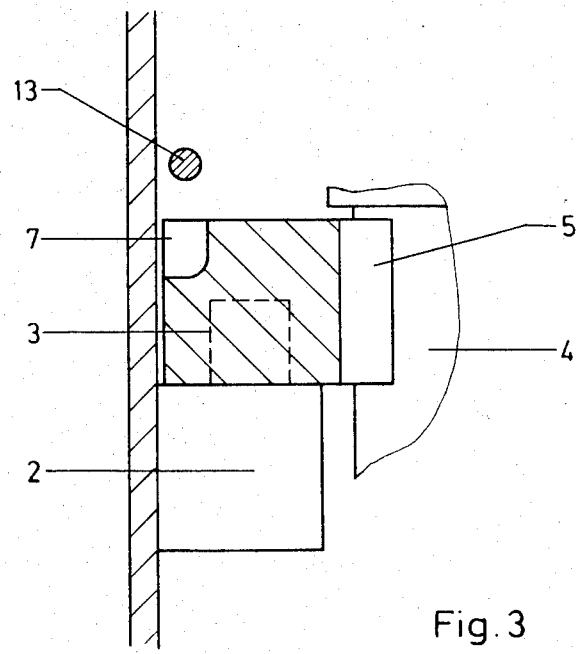
FIG. 3 is an enlarged sectional view taken along the lines C—D of FIG. 1.

According to FIGS. 1 and 3, two receiving parts 2 are arranged side by side on a case wall 1 of the anesthetizer, in which gas lines (not shown) terminate in plug junction 3. Evaporators 4 are placed with their connections in the extension parts 5 onto plug junction 3, and are secured against accidental loosening by bayonet catches 6 operated from the top. Extension parts 5 are provided on both sides with a recess 7.

Evaporators 4 carry on their topside each a scaled handwheel 8 with an attached annular disk 9. Disk 9 is traversed by an opening 10. A side pin 11 is inserted into each opening 10 and extends transverse to, and protrudes into, the interior of the opening 10.

An arm 12 is disposed between receiving parts 2, and it is secured to the case wall 1 and projects approximately to the center axis of the evaporator 4. Next to case wall 1, arm 12 is traversed by a set pin 13. At the free end of arm 12 is mounted in a crossbore 14 a longitudinally moving latch or bolt 15. The latch 15 is longer than the distance between disks 9 and 9 and it carries a journal or pin 16 which is guided in an oblong slot 17 of arm 12. The latch 15 is provided at its ends with longitudinal grooves 18 which receive the pin 11.

In the zero position of handwheel 8 of evaporators 4, latch 15 can enter the openings 10 of each disk 9 and the pins 11 are received by longitudinal grooves 18. In the center position of journal 16, both handwheels 8 are locked. When latch 15 is moved to the left with journal 16 in the represented manner, it leaves opening 10 of the right-hand evaporator 4 and its handwheel 8 is released for adjustment. As long as the right-hand handwheel is turned, latch 15 cannot be removed from opening 10 of the left-hand evaporator 4, and the latter remains locked. This is also true when the other end of opening 10 is aligned with latch 15 by a half turn, as shown since, in this position, pin 11 is displaced by 180° from the position shown in FIG. 1 in respect to longitudinal groove 18, and thus a displacement of latch 15 is prevented. The conditions are similar for using the left-hand evaporator 4. Each evaporator can be attached selectively to the receiving parts 2, 2, in the right or left position.

The anesthetizers contain generally two evaporators in which various anesthetics are evaporated, and the vapor is then fed in the adjusted amount to the respiratory system of the patient.

For safety reasons, it is necessary to use a locking mechanism which prevents the user from opening either the wrong evaporator or both evaporators.

The sealed handwheels 8 of evaporators 4 have in an attached annular disk 9 a through-opening 10, into the outer ends of which protrudes on the same side a pin 11. Between evaporators 4 is arranged in an arm 12 a latch 15 moving back and forth with its journal 16. One end of the arm 12 always engages an opening 10 of an associated right-hand or left-hand disk 10, depending on the position of journal 16. The latch 15 moves with its oblong slot 18 over pin 11 only when the associated disk 9 is properly directed so that its pin 11 does not block entry of the latch 15 into its opening 10. The corresponding handwheel 8, and thus evaporator 4, associated with disk 9, is locked, when the other disk 9 is released. In a center position of the latch 15, each end of the latch 15 must be accommodated within a respective opening 10 of each disk 9 and both handwheels of the two evaporators are locked.

While a specific embodiment of the invention has been shown and described in detail to illustrate the application of the principles of the invention, it will be understood that the invention may be embodied otherwise without departing from such principles.

What is claimed is:

1. A locking mechanism for use with two anesthetic evaporators, comprising first and second anesthetic evaporators, each evaporator having a rotatable opening valve disc, each disc having a radially extending opening therein, means for mounting said evaporators in side by side relationship such that said discs are separated by a predetermined distance and said respective radially extending openings are in alignment when rotated to face each other, an arm mounted to said mounting means and extending between said discs and having a transverse bore aligned with said respective radially extending openings when rotated to face each other, a cylindrical latch slidably mounted in said transverse bore and having a length slightly greater than said predetermined distance and an accommodation recess adjacent each end at a selected diametric location, a control pin mounted on each of said discs and entering into the opening of the associated disc at one diametric location, the distance between said control pins, when said openings are in alignment when rotated to face each other, being slightly greater than the length of said latch, each respective control pin being of a size to be accommodated within each respective accommodation recess of said latch when the opening of said disc and said control pin are aligned with the accommodation recess of said latch, said latch being positionable in said disc opening of either selected disc with the control pin being accommodated within the accommodation recess to lock the associated disk and to free the other disc for rotation for opening the associated evaporator, said latch also being positionable between said discs so that its respective ends enter into each of the openings of each of said discs to lock both of said disks.

2. A locking mechanism according to claim 1, including a journal mounted on said latch and extending outwardly therefrom, said arm having a slot in which said journal is movable between defined limits.

3. A locking mechanism according to claim 1, wherein said mounting means includes a wall structure on which said arm is rotated said wall structure having spaced receiving parts for said evaporators, said receiving part including an upright mounting pin, said evaporators having an extension part with a recess engageable over said mounting pin.

4. A locking mechanism according to claim 1, including a scaled handwheel mounted on each of said discs having graduations thereon for indicating the degree of opening of said opening valve disc.

* * * * *